United States Patent
Alharbi et al.

(10) Patent No.: US 11,806,790 B2
(45) Date of Patent: Nov. 7, 2023

(54) BIOSYNTHESIS OF METAL NANOPARTICLES

(71) Applicant: KING SAUD UNIVERSITY, Riyadh (SA)

(72) Inventors: Naiyf Sultan Helial Alaloi Alharbi, Riyadh (SA); Jamal Mohammed Ali Khaled, Riyadh (SA); Mohamed Salah El-Din Hodhud, Riyadh (SA); Shine Moosa Kadaikunnan, Riyadh (SA); Ahmed Saad Alobaidi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 736 days.

(21) Appl. No.: 16/716,449

(22) Filed: Dec. 16, 2019

(65) Prior Publication Data

US 2020/0377913 A1 Dec. 3, 2020

Related U.S. Application Data

(62) Division of application No. 16/423,532, filed on May 28, 2019, now Pat. No. 10,590,438.

(51) Int. Cl.
| | | |
|---|---|---|
| A01N 59/20 | (2006.01) | |
| A01N 25/12 | (2006.01) | |
| B22F 1/054 | (2022.01) | |
| B82Y 40/00 | (2011.01) | |
| B22F 9/24 | (2006.01) | |
| C12P 3/00 | (2006.01) | |
| C01G 3/10 | (2006.01) | |
| A01N 63/30 | (2020.01) | |

(52) U.S. Cl.
CPC .......... *B22F 9/24* (2013.01); *A01N 25/12* (2013.01); *A01N 59/20* (2013.01); *B22F 1/054* (2022.01); *C01G 3/10* (2013.01); *C12P 3/00* (2013.01); *B82Y 40/00* (2013.01); *C01P 2002/01* (2013.01); *C01P 2002/72* (2013.01); *C01P 2002/82* (2013.01); *C01P 2002/84* (2013.01); *C01P 2004/64* (2013.01)

(58) Field of Classification Search
CPC ......... A01N 59/20; A01N 25/12; A01N 63/30
See application file for complete search history.

(56) References Cited

U.S. PATENT DOCUMENTS

| | | | |
|---|---|---|---|
| 8,394,421 | B2 | 3/2013 | Mansoori |
| 8,465,721 | B2 | 6/2013 | Edwards et al. |
| 8,986,975 | B2 | 3/2015 | Mester et al. |
| 9,567,610 | B2 | 2/2017 | Castro Retamal et al. |
| 9,701,552 | B1 | 7/2017 | Ortashi et al. |

OTHER PUBLICATIONS

Chowdhury, M.N.K. et al., "Synthesis of copper nanoparticles and their antimicrobial performances in natural fibres," Materials Letters, vol. 98, pp. 26-29 (2013).*
Jones, E.B.G et al., "Classification of marine Ascomycota, Basidiomycota, Blastocladimycota and Chytridiomycota," Fungal Diversity, vol. 73, pp. 1-72 (2015).*
Kumar, S. et al., "MEGA X: Molecular evolutionary genetics analysis across computing platforms," Molecular Biology and Evolution, vol. 35(6), pp. 1547-1549 (2018).*
Wanasinghe, D.N. et al., "Phylogenetic revision of Camarosporium (Pleosporineae, Dothideomycetes) and allied genera," Studies in Mycology, vol. 87, pp. 207-256 (2017).*
Manceau et al., "Formation of metallic copper nanoparticles at the soil-root interface," Environmental science & technology 42.5 (2008): 1766-1772.
Varshney et al., "A Review: Biological Synthesis Of Silver And Copper Nanoparticles," Nano Biomedicine & Engineering, 2012, 4.2, 99-106.
Cuevas et al., "Extracellular Biosynthesis of Copper and Copper Oxide Nanoparticles by Stereum hirsutum, a Native White-Rot Fungus from Chilean Forests," Journal of Nanomaterials, 2015, 16.1, 57.
Thatoi et al., "Ecological role and biotechnological potential of mangrove fungi: a review", Mycology 2013, vol. 4, No. 1, pp. 54-71.
Siddiqui et al., "Fabrication of Metal Nanoparticles from Fungi and Metal Salts: Scope and Application", Nanoscale Research Letters (2016), 11:98, pp. 1-15.

* cited by examiner

*Primary Examiner* — John Pak
(74) *Attorney, Agent, or Firm* — Nath, Goldberg & Meyer; Richard C. Litman

(57) ABSTRACT

A method of preparing metal nanoparticles using a fungal extract includes providing an aqueous solution including a metal salt; and combining the fungal extract with the aqueous metal salt solution to produce the metal nanoparticles. The fungal extract can be an aqueous extract of the manglicolous fungi The metal salt can be copper sulfate ($CuSO_4$) and the metal nanoparticles can be copper nanoparticles. The metal nanoparticles can have a mean diameter in the range of from about 5 nm to about 100 nm. The copper nanoparticles can be used as an antimicrobial agent.

1 Claim, 5 Drawing Sheets

BIOSYNTHESIS OF METAL NANOPARTICLES

CROSS REFERENCE TO RELATED APPLICATION

This application is a divisional of application Ser. No. 16/423,532, filed May 28, 2019, now issued.

BACKGROUND OF THE INVENTION

1. Field of the Invention

The present invention relates to green synthesis of metal nanoparticles, particularly to synthesis of copper nanoparticles using a fungal extract.

2. Description of the Related Art

Nanotechnology is emerging as a rapidly growing field with its application in science and technology for the purpose of manufacturing new materials at the nanoscale level. Nanoparticles exhibit distinct or improved properties compared to their corresponding bulk materials. Because of their size, catalytic properties, ability to deliver drug, increased efficacy, and decreased toxicity, nanotechnology finds applications in various fields including healthcare, defense and day-to-day life. Because the nanoparticles possess a very high surface to volume ratio, they are particularly useful in applications where high surface areas are critical for success.

Green chemistry provides clean, nontoxic and eco-friendly methods of synthesizing metal nanoparticles using biological systems involving certain kinds of plants, algae, fungi and bacteria. (Nachiyar et al., 2015; Shende et al., 2017; Ottoni et al., 2017).

Metal nanoparticles have been used as antibacterial coatings in various medicinal materials and implants. For example, metal nanoparticles have been proven to be effective antibiotic delivery systems. The nanoparticles have also been used to prevent bacterial infections and detect bacteria in microbial diagnostics. As such, these nanoparticles can potentially provide effective antibiotic alternatives. As their mode of action is directed mainly to the bacterial cell wall, the nanoparticles will not be recognized by most antibiotic resistance mechanisms.

Thus, a method of producing metal nanoparticles utilizing a fungal extract thereby solving the aforementioned problems is desired.

SUMMARY OF THE INVENTION

A method of preparing metal nanoparticles using a fungal extract includes providing an aqueous solution including a metal salt; and combining the aqueous metal salt solution with a fungal extract to produce the metal nanoparticles. The fungal extract can be an aqueous extract of manglicolous fungi. The metal salt can be copper sulfate ($CuSO_4$) and the metal nanoparticles can be copper nanoparticles. The metal nanoparticles can have a mean diameter in the range of from about 5 nm to about 100 nm. The copper nanoparticles can be used as an antimicrobial agent.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figures 1A, 1B, 1C:
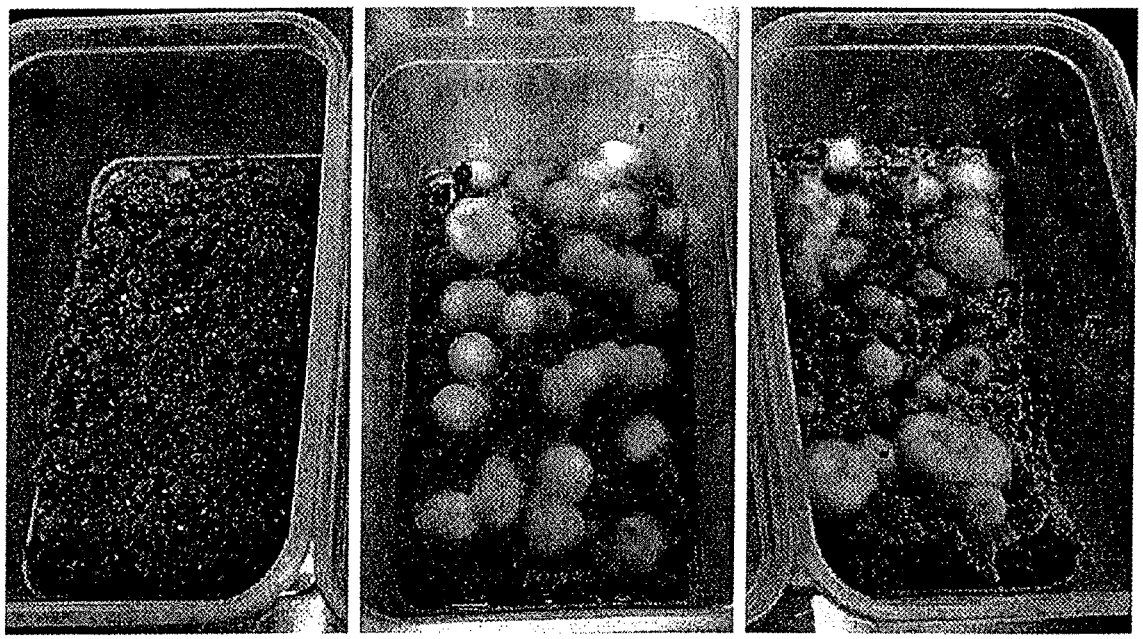
FIGS. 1A-1C are images after 2 weeks of (A) sterile sawdust control (no fungal growth) (B) inoculated sawdust treated with 50%:50% sterilized seawater:distilled water and (C) inoculated sawdust treated with sterilized distilled water.

A method for preparing metal nanoparticles includes combining an aqueous solution including a metal salt with a manglicolous fungal extract (e.g., *Ascocylindrica*) to produce the metal nanoparticles. The metal salt can be, for example, copper sulfate ($CuSO_4$) and the resulting metal nanoparticles can be copper nanoparticles. The aqueous solution of metal salt can be prepared by dissolving about 1 mL of mM/mL copper sulfate ($CuSO_4$) solution in about 50 ml of water. The manglicolous fungal extract can be an aqueous extract of *Ascocylindrica marina* (*A. marina*). The copper nanoparticles can have a mean diameter in the range of from about 5 nm to about 100 nm. The copper nanoparticles can be spherical, spheroidal, elongated spherical, rod-shaped, and/or faceted-shape. The copper nanoparticles can be used as an antimicrobial agent.

In an embodiment, *Ascocylindrica marina* (mycelia phase) can be first cultivated using a broth including yeast extract, glucose, malt extract, and water. The mycelia can be washed and a mycelia suspension can be prepared using sterile seawater or sterile distilled water. The suspension can be dispersed on a substrate to cultivate a fungal growth. The substrate may be a wood waste product. The wood waste product may be sterilized. Water may then be added to the fungal growth and the substrate to provide a mixture; and an aqueous extract of the fungal growth may be obtained by filtering the mixture.

As used herein, the term "nanoparticle" refers to a particle having at least one dimension and sized between 1 and 100 nanometers. The metal nanoparticles described herein can be copper nanoparticles. The copper nanoparticles can be from about 5 nm to about 100 nm in diameter, and may have a mean size from about 10 nm to about 30 nm in diameter. The copper nanoparticles can be effective as an antimicrobial.

The method of producing metal nanoparticles using a fungal extract is a green, simple, and cost effective method, which can easily be scaled up for large scale synthesis. The fungal extract can include an extract of manglicolous fungi. In an embodiment, the manglicolous fungi can be *Ascocylindrica marina*.

Manglicolous fungi are environmentally safe and non-pathogenic fungi. Accordingly, applications of manglicolous fungi on an industrial scale or for a medical application may be particularly fruitful. Manglicolous fungi are largely unexploited in industry and green chemistry applications, but, as the second largest ecological group inhabiting salt tolerant shrubs, ferns and palms, colonizing intertidal zones of mudflats and banks of tropical and subtropical rivers and coastlines in many parts of the world (Jones, 2000; Thatoi et al., 2013), they play a key role in nutrient recycling, through the degradation of lignocellulose materials of wood and leaf litter, as well as the decomposition of dead plant and animal parts (Jones et al., 2013).

The following examples will further illustrate the process of making the metal (copper) nanoparticles from a fungal extract.

Example 1

Preparing an Aqueous Fungal Extract (*Ascocylindrica*)

*Ascocylindrica marina*, an exemplary manglicolous fungi, was obtained in decaying submerged wood of mangroves in Tarot Island on the Arabian Gulf Coast of Saudi Arabia, identified based on its morphological characteristics based on the fruiting structures (ascomata, asci and ascospores) (Jones et al., 2015), and its identity confirmed by molecular identification based on the LSU ribosomal DNA, amplified using primers LROR and LR7 (Vilgalys & Hester 1990). Small subunit rDNA was amplified using NS1 and NS8 (White et al. 1990) primers. Sequencing was made by Macrogen Inc., Korea using MGTM Taq-HF DNA Polymerase, using the following cycling parameters: initial denaturation at 96° C. for 3 min, 96° C. for 15 s, 52° C. for 45 s, 72° C. for 1 min 30 s, and final elongation at 72° C. for 7 min. The resulting sequences were deposited at GenBank, and given accession numbers MK007123 for LSU rDNA and MK007124 for SSU rDNA. Phylogenetic analysis of the produced sequences was performed by MEGAX (Kumar et al., 2018). *Ascocylindrica marina* (*A. marina*) described in the present examples were cultivated using YMG broth (4 g yeast extract, 10 g glucose, 10 g malt extract in 1 liter 50% sea water; sterilized before use) until sufficient mycelium was formed in the growth media. The fungal spores were grown on the YMG agar at 22° C. for 14 days to produce a sterile mycelia phase.

The mycelium was then washed twice and a suspension of fungal spores was prepared. The mycelia were harvested from the surface of the YMG agar using sterile seawater mixed 1:1 with sterile distilled water or sterile distilled water alone to provide an inoculated sterile seawater suspension and inoculated sterile distilled water suspension, respectively. The total count of the fungi in each suspension was determined using agar-plate method according to (Clark, 1965), and adjusted to a final concentration of about $10^5$ CFU/mL.

Wood waste was used to grow the fungus used in the fungal extracts according to an embodiment of the present subject matter. In particular, wood waste of sawdust (non-limitingly, Teak wood) was collected from various carpenter shops located at the industrial area in Riyadh City, Saudi Arabia. One skilled in the art should understand that another substrate for growing fungus may be used, particularly having common components of lignin and poly-carbohydrates including glucose, xylose, mannose, arabinose, galactose and rhamnose. The wood waste was autoclaved at 121° C. for 15 minutes to eliminate unwanted biocontaminants. A layer of sawdust was then placed in plastic boxes that had been sterilized using 70% ethanol solution. The sterile plastic boxes containing sterile sawdust were moistened with about 50 mL of one of the inoculated sterile distilled water suspension, prepared as above; the inoculated sterile seawater suspension, prepared as above; sterile distilled water without inoculation (control group 1); or sterile seawater mixed 1:1 with sterile distilled water without inoculation (control group 2) (FIG. 1).

Aqueous extracts were obtained by adding 100 mL of sterile distilled water to each box containing cultivated mycelia of *A. marina* and sawdust. The mixture was transferred to a sterile conical flask and then mixed using a shaker on 200 rpm at 25° C. for 12 h. A resulting aqueous extract was removed from mycelia and sawdust by filtration using a 0.65 µm pore size membrane filter. A control extract was prepared from each of the control groups by the same procedure as above.

The resultant filtrate extract of *A. marina* was kept in a refrigerator (4° C.) until use.

Example 2

Synthesis of Copper Nanoparticles

Copper nanoparticles were synthesized by preparing 100 mL of $CuSO_4.5H_2O$ solution (1 mM) in an Erlenmeyer flask (250 mL), and then adding 1 mL of the exemplary aqueous extracts prepared as above to the Erlenmeyer flask to provide a mixture. The mixture was incubated at 25° C. for 24 h in a shaking incubator, with shaking at 180 rpm. The primary monitor of synthesis of copper nanoparticles was visual change in color to brown. Any other appropriate means of monitoring the production of copper nanoparticles may be used. When a substantial synthesis of copper nanoparticles was achieved, the copper nanoparticles were isolated by centrifugation at 1500 rpm for 30 min. The resulting pellets were collected and washed three times with distilled water.

Example 4

Characterization of the Copper Nanoparticles

Characterization of the synthesized copper nanoparticles was performed using an ultraviolet/visible spectrophotometer (UV-1800 Shimadzu spectrophotometer, Japan), Fourier Transform Infrared Spectroscopy (Perkin-Elmer 1000 FT-IR, United States of America), transmission electron microscopy (JEOL-JEM-1011, Tokyo, Japan), and X-Ray Diffraction (XRD-Ultima IV Rigaku, United States of America). (Dhas, et al., 1998; Khanna et al., 2007).

The UV-visible spectra, X-ray diffraction (XRD) and transmission electron microscopy (TEM) tests confirmed production of copper nanoparticles (see FIGS. 2-5). Aqueous solution extracted from control groups demonstrated no ability to synthesize copper nanoparticles according to color changes and UV-visible spectra (FIG. 2), confirming that the aqueous fungal extract facilitates synthesis of the copper nanoparticles.

Figure 2:
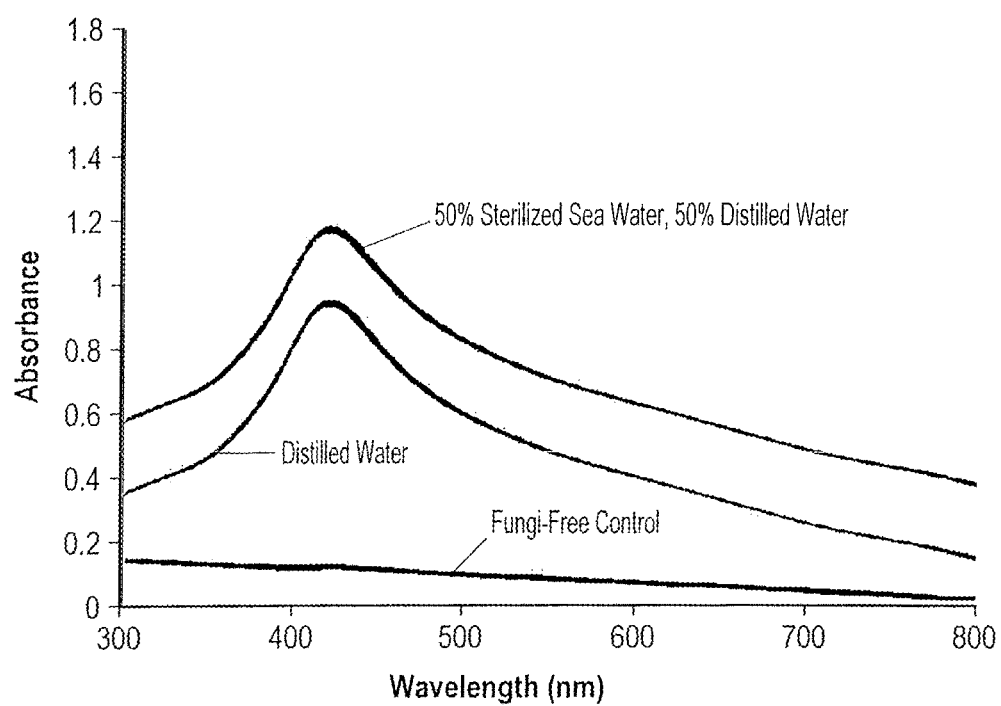
FIG. 2 is a plot of UV-Visible spectra of copper nanoparticles synthesized as disclosed herein by addition of 1 mL of 1 mM copper precursor to the aqueous extract including fungi grown in sawdust treated with 50%:50% sterilized seawater:distilled water or distilled water, and a sterilized sawdust control.
Figure 3:
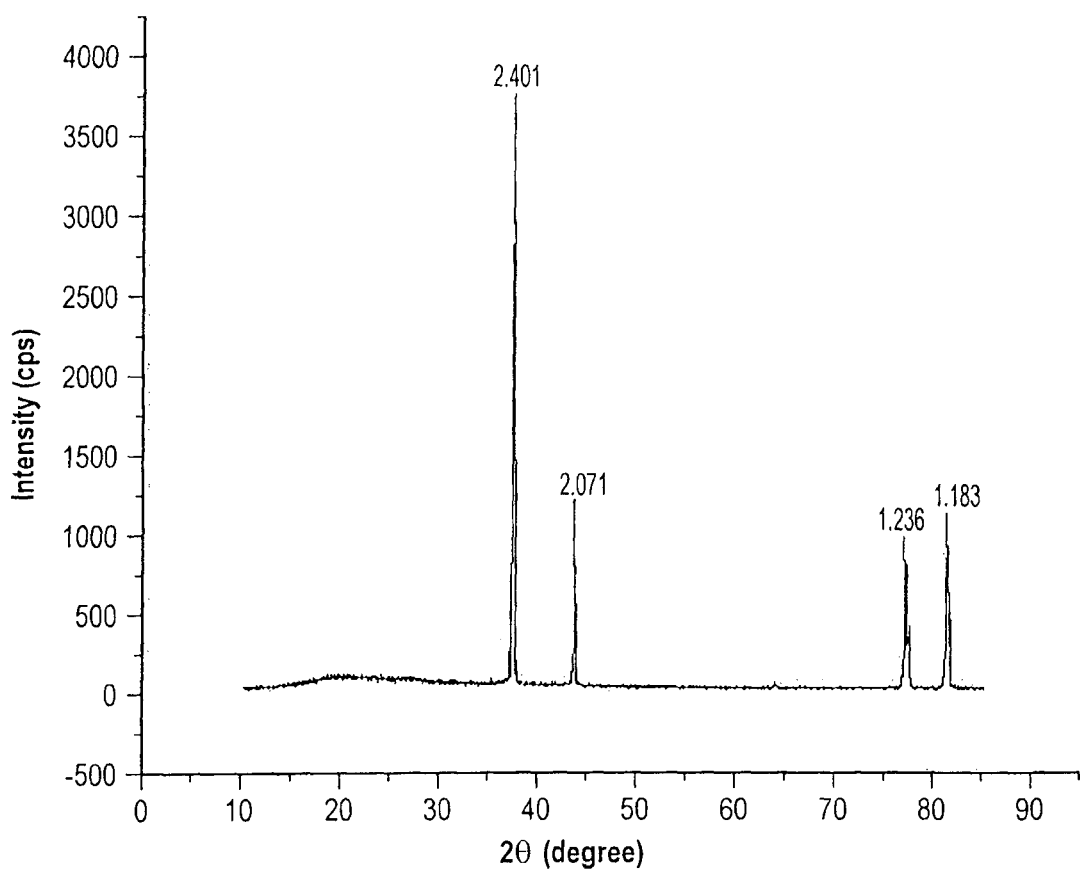
FIG. 3 is a graph showing X-ray diffraction (XRD) of copper nanoparticles synthesized according to the present method, showing diffraction peaks corresponding to the characteristic face centered cubic (FCC) copper lines indexed as (2.401), (2.071), (1.236) and (1.183) at diffraction angles of 37.3°, 44.2°, 76.5° and 82.8°, respectively.
Figure 4:
FIG. 4 shows a transmission electron microscopy (TEM) micrograph of copper nanoparticles synthesized according to the present subject matter. The copper nanoparticles typically have an elongated, or "spike", shape with mean size of about 18 nm.
Figure 5:
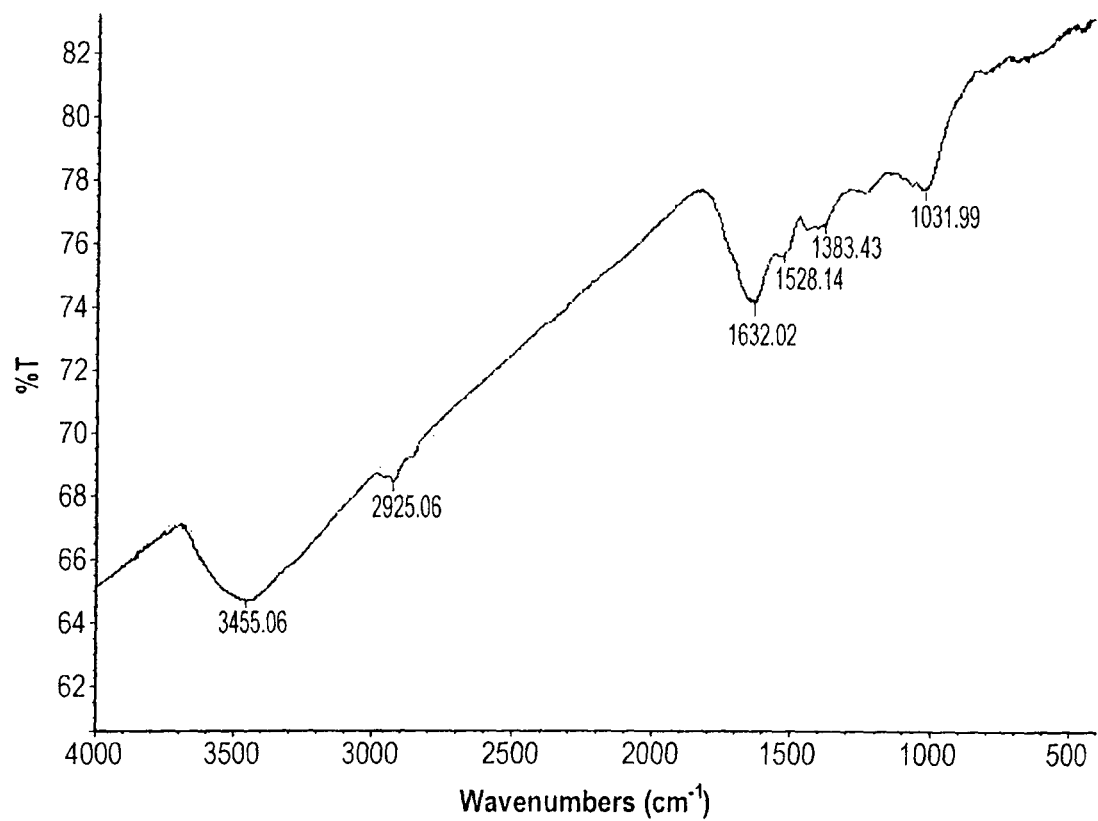
FIG. 5 shows a Fourier-transform infrared spectrum (FTIR) of the exemplary synthesized copper nanoparticles

The maximum absorbance of the as-synthesized copper nanoparticles at 430 nm, which occurs as a single peak in the visible region, indicates stable and well-dispersed copper nanoparticles resulting from the presently disclosed method (FIG. 2). The mono-disperse copper nanoparticles prepared in the present examples have a mean diameter of around 18-20 nm diameter and are typically elongated, according to TEM and XRD analyses (FIGS. 3-4). FTIR analysis shows peaks at 3455, 2925, 2632, 1383, 1031 cm$^{-1}$, indicating the existence of capping agents around the copper nanoparticles (FIG. 5).

Example 4

Antimicrobial Activity Study

Antimicrobial activity of the copper nanoparticles was tested against antibiotic susceptible and resistant bacteria using a two-fold microdilution assay (Abb, 2002) to determine a minimal inhibitory concentration (MIC) of the synthesized copper nanoparticles for each bacterial strain tested. Each bacterial strain was cultivated in 20 mL of sterile nutrient broth prepared according to manufactures' directions and then sterilized at 121° C. for 10 min. Each bacterial strain was cultivated at 37° C. for 24 h, and the resulting bacterial suspension was prepared to obtain an optical density of 0.65 at 560 nm, determined by spectrophotometer (ELx800 microplate reader (Bio TeK, USA)). Each well of a 96 well microplate received 90 µL of sterile nutrient broth with 10 µL of the bacterial suspension. Serial dilutions were prepared using successive two-fold dilutions from the copper nanoparticles stock solution (1200 µg/mL copper nanoparticles in solution, e.g., sterile water). For example, a first well in microplate received 100 µl of the copper nanoparticles solution (resulting in 600 µg/mL), then 100 µl was transferred into a second well from the first well, and the process continued to the last well in the row. Finally, 100 µl removed from the final well was disposed in 70% ethanol solution. For the control groups, sterile distilled water was used instead of the copper nanoparticles.

The microplates were incubated at 37° C. for 19 h. The bacterial growth was determined by microplate reader at 560 nm, compared with control groups. The minimal inhibitory concentrations were calculated from the wells that had an optical density similar to the control groups.

Figure 6:
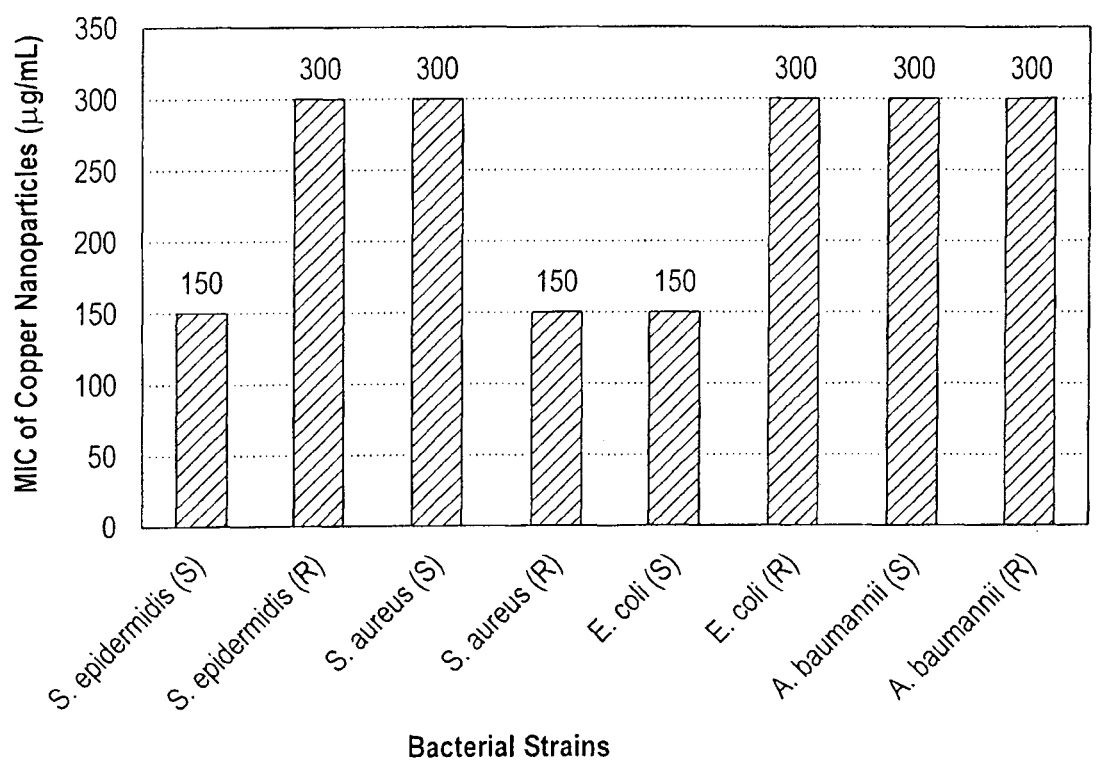
FIG. 6 shows the minimal inhibitory concentration (MIC) of the synthesized copper nanoparticles against a variety of bacterial strains. S indicates susceptibility to antibiotics and R indicates resistance to antibiotics (N=2).

FIG. 6 confirms that the copper nanoparticles synthesized as described above have antibacterial activity. Both antibiotic resistant bacterial strains and susceptible bacterial strains were inhibited by the copper nanoparticles. The minimal inhibitory concentrations of the copper nanoparticles ranged from about 150 to 300 µg/mL. Development of bacterial resistance to antibiotics limits the ability of standard antibiotics in treating bacterial infections. Copper nanoparticles have been shown to inhibit several pathogenic bacteria, including *S. aureus*, methicillin-resistant *S. aureus* (MRSA), *S. epidermidis, E. coli*, and *Pseudomonas aeruginosa* with minimal bactericidal concentrations ranging from 100 mg/ml to 5000 mg/ml (Ren et al., 2009; Hajipour et al., 2012). The copper nanoparticles obtained according to the present teachings inhibited at least *S. epidermidis* (S), *S. epidermidis* (R), *S. aureus* (S), *S. aureus* (R), *E. coli* (S) *E. coli* (R), *A. baumannii* (S) and *A. baumannii* (R) with minimal bactericidal concentrations ranging from 300 to 600 µg/mL (FIG. 6). Table 1 shows the bacterial strains used in the present examples, and identifies the bacterial strains resistant and/or susceptible to the antibiotics.

TABLE 1

Bacterial strains and results of susceptibility tests

| | Susceptibility test of Gram positive Bacteria | | | |
| --- | --- | --- | --- | --- |
| Antibiotics | *S. epidermidis* (R) | *S. epidermidis* (S) | *S. aureus* (S) | MRSA |
| Gentamycin | R | S | S | S |
| Imipenem | R | S | S | R |
| Cefoxitin | R | S | Negative. | Positive. |
| Cefotaxime | R | N.T | N.T | N.T |
| Ampicillin | R | S | BLAC | BLAC |
| Penicillin G | R | S | BLAC | BLAC |
| Oxacillin | R | S | S | R |
| Amoxicillin-Clavulanate | R | S | S | R |
| Trimethoprim-Sulfamethoxazole | R | S | S | S |
| Clindamycin | R | S | S | N.T |
| Erythromycin | R | S | R | N.T |
| Mupirocin High level | R | N.T | N.T | N.T |
| Mupirocin | N.T | S | S | S |
| Ciprofloxacin | R | S | S | S |

| | Susceptibility test of Gram negative Bacteria | | | | |
| --- | --- | --- | --- | --- | --- |
| Antibiotics | *E. coli* (R) | *E. coli* (S) | Antibiotics | *A. baumannii* (R) | *A. baumannii* (S) |
| Amoxicillin | R | S | Amoxicillin | R | S |
| Ampicillin | R | S | Ampicillin | R | N.T |
| Cefalotin | R | S | Amoxicillin/Clavulanic acid | R | N.T |
| Cefuroxime | R | N.T | Cefuroxime | R | S |
| Cefixime | R | S | Cefoxitin | R | N.T |
| Aztreonam | R | S | Cefixime | R | N.T |
| Amoxicillin | R | S | Cefotaxime | R | S |
| | | | Ciftriaxone | R | N.T |
| | | | Aztreonam | R | N.T |
| | | | Nitrofurantoin | R | N.T |

*MRSA = Methicillin-resistant *S. aureus*, R = resistant, S = susceptible, N.T = Not tested and BLAC = Beta-lactamase positive.

It is to be understood that the present method is not limited to the embodiments described above, but encompasses any and all embodiments within the scope of the following claims.

We claim:

1. A method of inhibiting growth of a microorganism, comprising the steps of:
   preparing an aqueous extract of *Ascocylindrica marina*, wherein the aqueous component is selected from the group consisting of sterile seawater mixed 1:1 with sterile distilled water or sterile distilled water alone;
   providing an aqueous solution including a metal salt, wherein the metal salt is copper sulfate ($CuSO_4$) and the aqueous component is water, wherein the aqueous copper salt solution has a copper sulfate ($CuSO_4$) concentration of 1 mM;
   combining the aqueous extract of the *Ascocylindrica marina* with the aqueous copper sulfate ($CuSO_4$) solution to produce a mixture;
   incubating the mixture at 25° C. for 24 h in a shaking incubator, with shaking at 180 rpm to produce copper nanoparticles, wherein the copper nanoparticles have a mean diameter in the range of from 10 nm to 30 nm;
   isolating the copper nanoparticles; and
   contacting the microorganism with the copper nanoparticles.

* * * * *